US007722700B2

(12) United States Patent
Sprinkle (10) Patent No.: US 7,722,700 B2
(45) Date of Patent: May 25, 2010

(54) APPARATUS AND METHOD OF PROVIDING CONCENTRATED PRODUCT GAS (75) Inventor: Thomas Sprinkle, Rocky River, OH (US)

(73) Assignee: Invacare Corporation, Elyria, OH (US)

(*) Notice: Subject to any disclaimer, the term of this patent is extended or adjusted under 35 U.S.C. 154(b) by 693 days.

(21) Appl. No.: 11/522,683

(22) Filed: Sep. 18, 2006

(65) Prior Publication Data
US 2008/0066616 A1   Mar. 20, 2008

(51) Int. Cl.
B01D 53/02   (2006.01)
(52) U.S. Cl. ............... 95/22; 95/23; 95/96; 95/148; 96/113; 96/130; 96/421; 96/422; 128/205.12; 128/205.27
(58) Field of Classification Search ............ 95/22, 95/23, 96, 148; 96/113, 130, 417, 422, 421; 128/204.21, 204.22, 205.12, 205.27
See application file for complete search history.

(56) References Cited

U.S. PATENT DOCUMENTS

| | | | |
|---|---|---|---|
| 4,449,990 A | 5/1984 | Tedford, Jr. | |
| 4,561,287 A | 12/1985 | Rowland | |
| 4,826,510 A | 5/1989 | McCombs | |
| 4,932,402 A | 6/1990 | Snook et al. | |
| 4,971,609 A | 11/1990 | Pawlos | |
| 5,099,837 A | 3/1992 | Russel et al. | |
| 5,258,056 A * | 11/1993 | Shirley et al. | 95/22 |
| 5,626,131 A | 5/1997 | Chua et al. | |
| 5,720,276 A | 2/1998 | Kobatake et al. | |
| 5,906,672 A | 5/1999 | Michaels et al. | |
| 5,917,135 A | 6/1999 | Michaels et al. | |
| 5,988,165 A | 11/1999 | Richey, II et al. | |
| 6,427,690 B1 | 8/2002 | McCombs et al. | |
| 6,520,176 B1 | 2/2003 | Dubois et al. | |
| 6,629,525 B2 | 10/2003 | Hill et al. | |
| 6,651,658 B1 | 11/2003 | Hill et al. | |
| 6,691,702 B2 | 2/2004 | Appel et al. | |

(Continued)

FOREIGN PATENT DOCUMENTS

EP   1661596   5/2006

(Continued)

OTHER PUBLICATIONS

Invacare Oxygen Products (Company Brochure) Form No. 05-054, Copyright 2005.

(Continued)

Primary Examiner—Robert A Hopkins
(74) Attorney, Agent, or Firm—Calfee, Halter & Griswold LLP (57) ABSTRACT Component gas is separated from a gas mixture. Component gas flow rate, or demand, is determined. One or more gas separator operating parameters is changed based on the component gas flow rate. For example, gas flow rate can be approximated by measuring a rate of pressure decay of a product tank during a time period in which the tank is not being replenished by the separating system. When it is determined that the flow rate is relatively low, operating parameters of the separating system are changed to improve system performance with the lower demand. For example, a target product tank pressure at which sieve beds are switched can be lowered when demand is lower.

23 Claims, 4 Drawing Sheets

U.S. PATENT DOCUMENTS

| | | | |
|---|---|---|---|
| 6,764,534 | B2 | 7/2004 | McCombs et al. |
| 6,949,133 | B2 | 9/2005 | McCombs et al. |
| 7,329,304 | B2 | 2/2008 | Bliss et al. |
| 7,445,663 | B1 * | 11/2008 | Hunter et al. .......... 95/96 |
| 2002/0053286 | A1 | 5/2002 | Czabala |
| 2004/0079359 | A1 | 4/2004 | Aylsworth et al. |
| 2006/0086251 | A1 | 4/2006 | Sprinkle |
| 2008/0066616 | A1 | 3/2008 | Sprinkle |

FOREIGN PATENT DOCUMENTS

| | | |
|---|---|---|
| WO | WO2008036159 | 3/2008 |

OTHER PUBLICATIONS

International Search Report and Written Opinion from PCT/US2007/018468, mailed Feb. 11, 2008.

Office action from U.S. Appl. No. 11/258,480, mailed Feb. 12, 2008.

Int'l App. No. PCT/US08/61022, Int'l Search Report, 2 pages, mailed Jul. 18, 2008.

Int'l App. No. PCT/US08/61022, Written Opinion of the Int'l Searching Authority, 5 pages, mailed Jul. 18, 2008.

Invacare Corporation, Oxygen Products Brochure, Form No. 05-054, Copyright 2005.

Invacare Corporation, Oxygen Products Brochure, Form No. 05-054, Copyright 2008.

Invacare Corp., XP02 Portable Concentrator, Invacare Product Catalog, www.invacare.com/ cgi-bin/ imhqprd/inv_catalog/prod_cat_detail.jsp!s=0 & prodID=XPO100 & catOID=536885301, printed Mar. 17, 2008, 1 page (2008).

* cited by examiner

APPARATUS AND METHOD OF PROVIDING CONCENTRATED PRODUCT GAS

BACKGROUND

Various applications exist for the separation of gaseous mixtures. For example, the separation of nitrogen from atmospheric air can provide a highly concentrated source of oxygen. These various applications include the provision of elevated concentrations of oxygen for medical patients and flight personnel. Hence, it is desirable to provide systems that separate gaseous mixtures to provide a concentrated product gas, such as a breathing gas with a concentration of oxygen.

Several existing product gas or oxygen concentrators, for example, are disclosed in U.S. Pat. Nos. 4,449,990, 5,906,672, 5,917,135, and 5,988,165 and U.S. patent application Ser. No. 11/258,480 filed Oct. 25, 2005, which are commonly assigned to Invacare Corporation of Elyria, Ohio and fully incorporated herein by reference in their entirety for all purposes. In general, these concentrators produce concentrated oxygen by passing pressurized ambient air through one of a pair of pressure swing adsorption sieve beds. The sieve beds contain Zeolite media. Zeolite is a clay-like substance that is processed to form small holes in the media pellets. As ambient air passes over the Zeolite, nitrogen atoms are trapped in the holes leaving oxygen mixed with small amounts of other gases found in the air such as argon, neon, and xenon. Typically the oxygen content of air produced by a concentrator consists of about 95% oxygen. As more air is treated by the sieve bed the holes in the media pellets become clogged with nitrogen atoms and eventually will no longer effectively remove nitrogen from the air. Prior to this exhaustion of Zeolite, the concentrator switches operation to the other sieve bed and flushes the exhausted bed with concentrated gas from the newly activated bed. This cycling of active sieve beds continues during operation of the concentrator.

SUMMARY

Methods and apparatuses for providing a concentrator product gas are provided. In one embodiment, component gas is separated from a gas mixture. Component gas flow rate, or demand, is determined. One or more gas separator operating parameters is changed based on the component gas flow rate. For example, gas flow rate can be approximated by measuring a rate of pressure decay of a product tank during a time period in which the tank is not being replenished by the separating system. When it is determined that the flow rate is relatively low, operating parameters of the separating system are changed to improve system performance with the lower demand. For example, a target product tank pressure at which sieve beds are switched can be lowered when demand is lower.

DESCRIPTION

Prior to discussing the various embodiments, a review of the definitions of some exemplary terms used throughout the disclosure is appropriate. Both singular and plural forms of all terms fall within each meaning:

"Logic," as used herein, includes but is not limited to hardware, firmware, software and/or combinations of each to perform a function(s) or an action(s), and/or to cause a function or action from another component. For example, based on a desired application or needs, logic may include a software controlled microprocessor, discrete logic such as an application specific integrated circuit (ASIC), or other programmed logic device. Logic may also be fully embodied as software.

"Software," as used herein, includes but is not limited to one or more computer readable and/or executable instructions that cause a computer or other electronic device to perform functions, actions, and/or behave in a desire manner. The instructions may be embodied in various forms such as routines, algorithms, modules or programs including separate applications or code from dynamically linked libraries. Software may also be implemented in various forms such as a stand-alone program, a function call, a servlet, an applet, instructions stored in a memory, part of an operating system or other type of executable instructions. It will be appreciated by one of ordinary skill in the art that the form of software is dependent on, for example, requirements of a desired application, the environment it runs on, and/or the desires of a designer/programmer or the like.

Industry standard home oxygen concentrators utilize Pressure Swing Adsorbtion (PSA) technology to separate oxygen from the other constituents of room air—the most prevalent being nitrogen. Room air is pumped through a pneumatic network by an air compressor. The air compressor is generally AC powered and lacks speed control. Some commercially available home oxygen concentrators utilize time-based control while others utilized pressure based control. The home oxygen concentrators with AC powered compressors all operate independent of oxygen demand or output. The concentrators are controlled in a manner that is optimized for the best oxygen production at the maximum rated flow for the unit. The most common maximum rated flow rate for a home oxygen concentrator is five liters per minute. However, the majority of patients using concentrators are on prescriptions of three liters per minute or less. Therefore, concentrators that operate to provide the maximum rated flow rate at all times regardless of the actual flow rate are usually over-working the compressor and pneumatic components. For example, when the concentrator is operated to provide five liters per minute, the compressor is required to pressurize the product tank to a level (21 psi in standard concentrators) to provide the maximum rated flow rate even though a lower product tank pressure would be adequate to supply the actual flow rate required by the patient. This in turn results in elevated energy consumption, heat generation, noise, and component wear.

Figure 1:
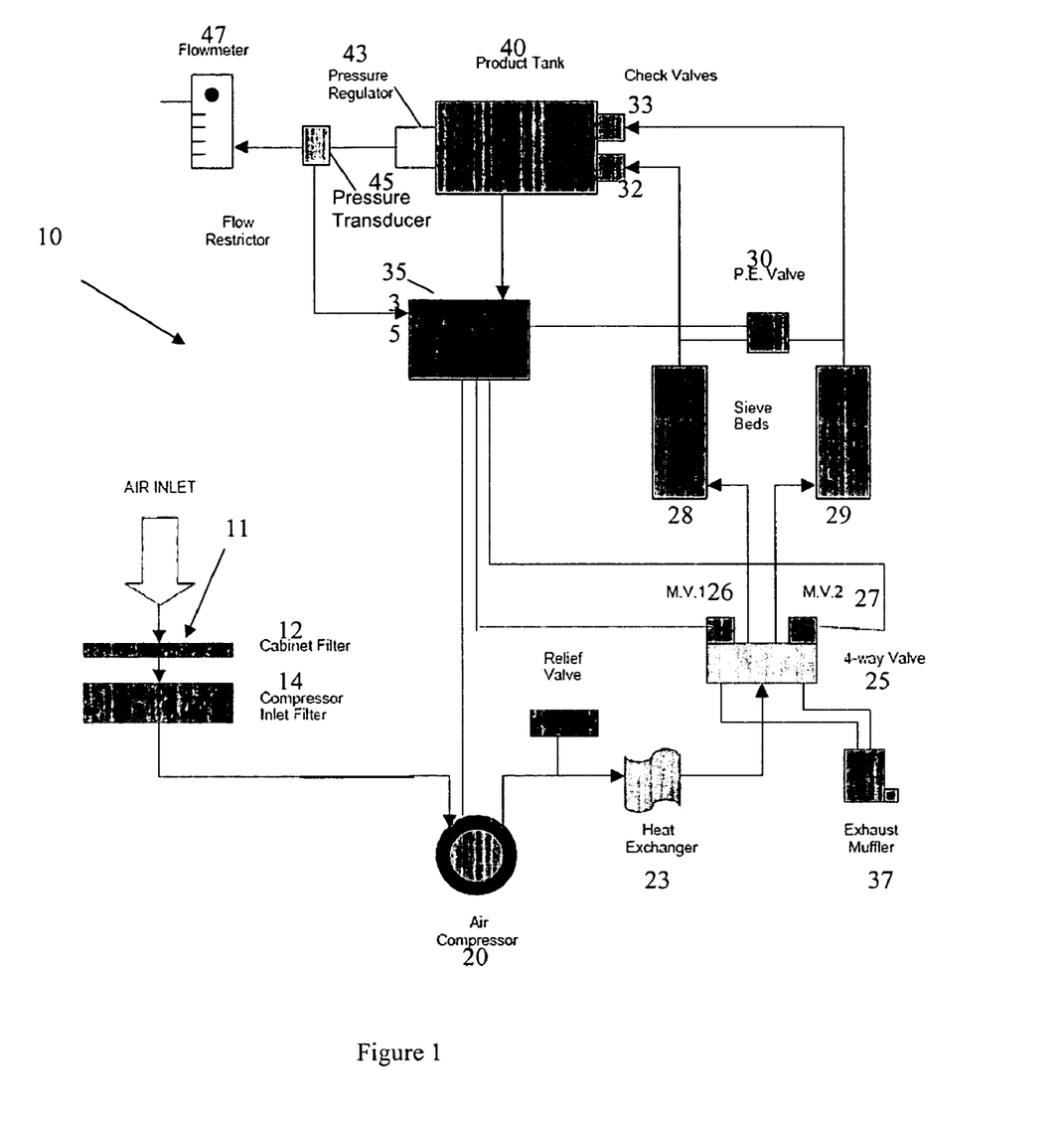
FIG. 1 is a schematic diagram of an oxygen concentrator constructed in accordance with an embodiment of the present invention.

FIG. 1 is a schematic diagram of an exemplary oxygen concentrator 10. The oxygen concentrator 10 that is described herein is just one example of an oxygen concentrator and all of the components described below need not be present in all embodiments of the present invention. Air comes into the concentrator through an air inlet 11 and is filtered by a cabinet filter 12 that removes large particles and a compressor inlet filter 14 that removes smaller particles such as dust. An air compressor 20 compresses the air to pressurize it. A pressure relief valve 21 is placed downstream from the compressor to reduce the risk of damage to the compressor in the event the concentrator air flow pathway becomes obstructed. A heat exchanger 23 cools the air that has been heated due to compression.

Cooled, compressed air passes to a four way valve 25 that is controlled by two solenoid operated pilot valves referred to as a first main valve 26 and a second main valve 27. The solenoid valves are actuated by a controller 35. The four way valve routes the cooled, compressed air through one of two PSA sieve beds 28, 29. From the beds, the concentrated gas flows to one of two check valves 32, 33 and to a product tank. The check valves prevent air from the tank from flowing back into the sieve beds and concentrated gas being supplied by the active bed must reach a threshold pressure to move through the check valve into the tank. A pressure regulator 43 controls the pressure at which concentrated oxygen is passed from the tanks. A pressure transducer 45 measures a tank pressure and feeds this information to the controller 35. A flow meter provides a visual indication to the patient of the flow rate of concentrated gas from the concentrator.

Figure 2:
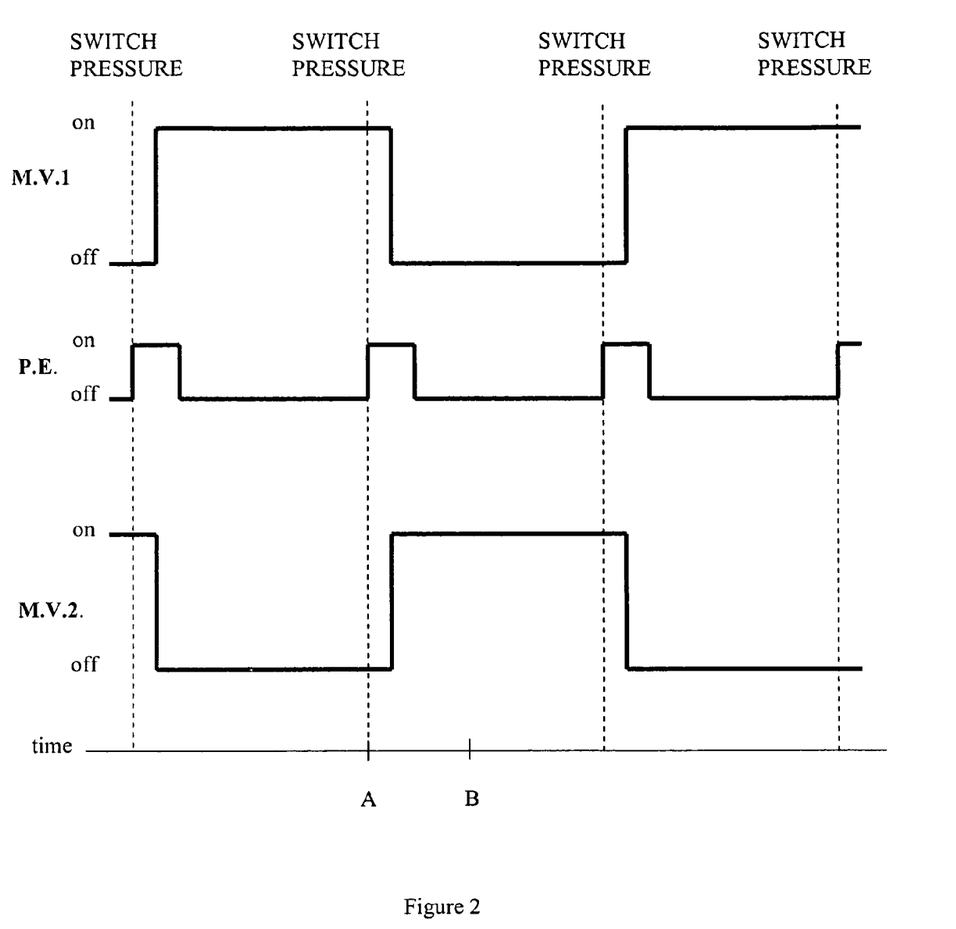
FIG. 2 is a timing diagram that shows the operation of valve components of the oxygen concentrator shown in FIG. 1.

During operation of the concentrator, the controller controls the actuation of the four way valve's solenoids 26, 27 and a pressure equalization valve 30 that selectively connects the outlets of the two sieve beds 28, 29 to one another. FIG. 2 outlines the timing of the various valve actuations that are performed to pass room air alternately through one of the two sieve beds and to periodically purge and switch to an inactive sieve bed as will be described in more detail below. The operation of the valves is based on a product tank pressure. This product tank pressure is determined based on an expected flow rate, which in the past has been a single flow rate, the maximum rated flow rate.

Referring to FIG. 2 in addition to FIG. 1 the operation of concentrator, particularly with respect to the actuation of the first and second main valves and the pressure equalization valves, is outlined. Beginning at the left of the timing diagram in FIG. 2, for the purposes of this discussion, the concentrator begins operation with the pressure equalization valve opening to connect the outlets of the sieve beds to one another. This allows product gas from the active sieve bed (in this case the second bed 29) to pressurize the inactive sieve bed (first bed 28). After a delay, the first main valve 26 (MV1) is opened to connect the pressurized air from the compressor to the first sieve bed 28. Simultaneously, the second main valve 27 is connected to an exhaust muffler 37 and vents to atmosphere through the muffler. The product gas flowing through the second sieve bed and out through the muffler collects trapped nitrogen atoms within the second sieve bed and carries them out of the sieve bed.

After a delay, the PE valve is closed and product gas begins to build pressure at check valve 32 until it overcomes the threshold pressure of the valve and enters the product tank. The first main valve remains open until pressure at the product tank reaches a "switch" pressure, for example 21 psi. When the product pressure reaches the switch pressure, the PE valve is opened, connecting the inlet of the first sieve bed to the exhaust muffler 37 and out to ambient air. The first sieve bed is then pressurized with the product gas that was building up at the outlet of the second sieve bed due to the opening of the PE valve. After a delay, the second main valve is opened and connects the outlet of the second sieve bed to the check valve 33 and the product tank 40. After flushing the first sieve bed for a period of time, the PE valve closes. This cycling process repeats during operation of the concentrator.

As already discussed in the background the switch pressure is selected based on the maximum rated flow rate of, in this case, five liters per minute. Since the majority of the time, a concentrator will be called on to produce only about three liters per minute, it is possible to reduce the switch pressure to a lower value, for example, 10-20 psi, and preferably 16 psi when the concentrator is experiencing this lower demand. The concentrator can be placed in a "conservation mode" in which the bed switching cycle is triggered by the lower pressure of 16 psi. In higher flow operating conditions, the concentrator transitions to a "high performance mode" in which the operation sequence of the concentrator does not change from that shown in FIG. 2, but the switch pressure is set to a higher pressure such as 20-25 psi, but preferably 21 psi.

The flow rate of gas being consumed by the patient can be determined in a number of ways. For example, a flow meter capable of sending signals to the controller could monitor the gas leaving the tank. An ultrasonic oxygen sensor can be used to detect a flow rate. The method employed in the described concentrator measures pressure decay at the tank (with pressure transducer 45 in FIG. 1) during the time in which the patient is consuming gas and the check valve has not yet allowed gas from the active sieve bed enter the tank. For example, pressure readings can be taken at points "A" and "B" on FIG. 2. The first pressure reading A is immediately after the PE valve is opened at which time gas stops flowing into the product tank. The second reading B is taken after the PE valve is closed but prior to pressure of product gas from the newly activated sieve bed overcoming the threshold of the check valve. The pressure decay during this time is due to patient demand and therefore gives a good indication of the present demand. This method of detecting flow rate is also described in U.S. patent application Ser. No. 11/258,480 that is identified in the background.

Figure 3:
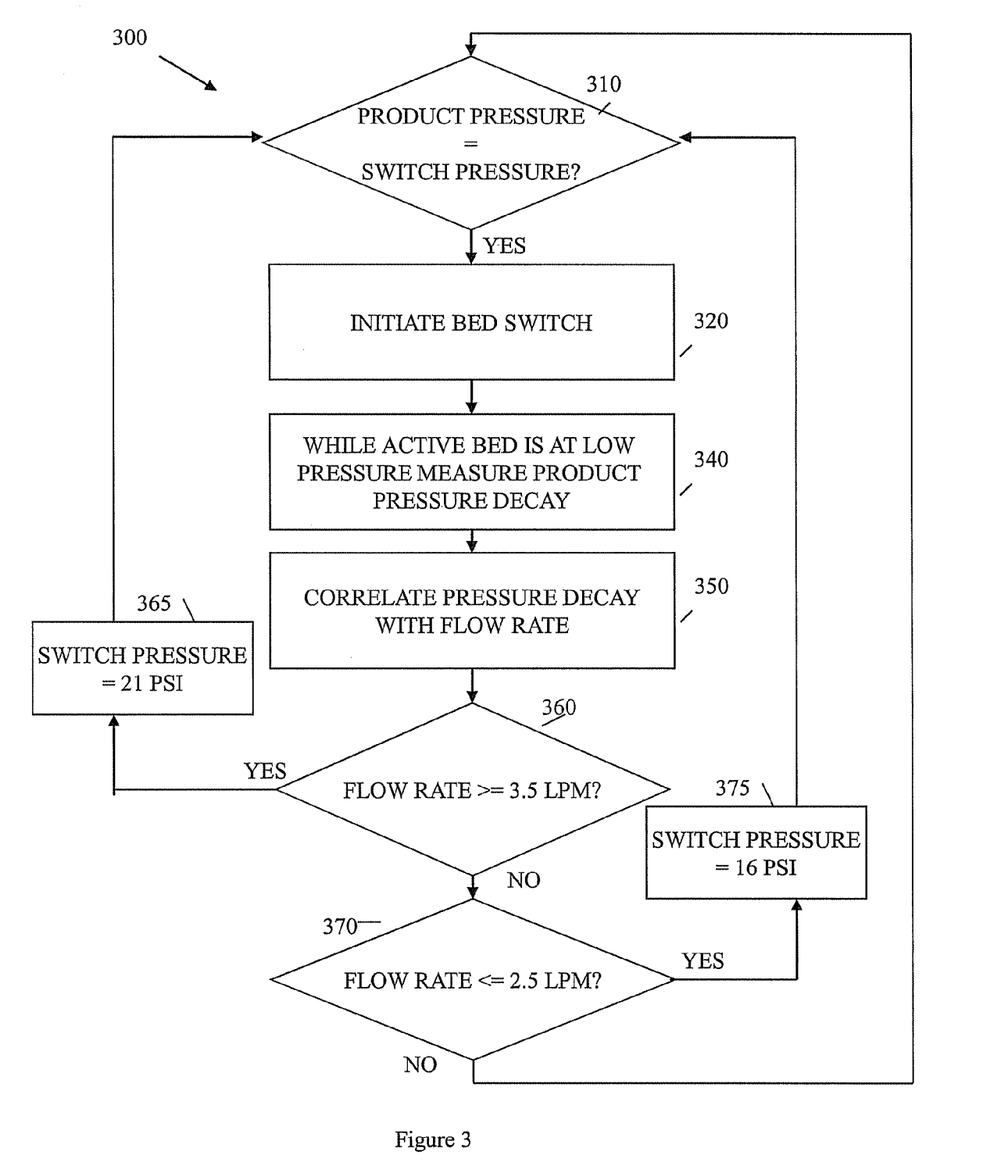
FIG. 3 is a flowchart that outlines a procedure for operation of the oxygen concentrator of FIG. 1.

Referring now to FIG. 3, the operation of the concentrator will be described with reference to the flowchart illustrated therein. In the flowchart, the rectangular elements denote processing blocks and represent software instructions or groups of instructions. The quadrilateral elements denote data input/output processing blocks and represent software instructions or groups of instructions directed to the input or reading of data or the output or sending of data. The flow diagrams shown and described herein do not depict syntax of any particular programming language. Rather, the flow diagrams illustrate the functional information one skilled in the art may use to fabricate circuits or to generate software to perform the processing of the system. It should be noted that many routine program elements, such as initialization of loops and variables and the use of temporary variables are not shown.

FIG. 3 outlines a procedure 300 for operating a concentrator to automatically place the concentrator in conservation mode when demand is relatively low, such as less than 2.0-3.0 liters per minute, and preferably less than 2.5 liters per minute. The concentrator is placed in high performance mode when the demand is relatively high, such as more than 3.5-4.5 liters per minute, and preferably 3.5 liters per minute. At 310, the product tank pressure is compared to the switch pressure, which is set to either 21 or 16 psi. Once the product pressure reaches the switch pressure at 320 the bed switch is initialized by opening the PE valve. Product pressure decay is measured during the time prior to opening of the check valve at 340 and at 350, the pressure decay is correlated to a flow rate, using, for example a look up table stored in the controller. At 360, the flow rate is compared to 3.5 liters per minute and if the flow rate is above 3.5 liters per minute, the switch pressure is set to 21 psi. At 370 the flow rate is compared to 2.5 liters per minute and if it is less than 2.5 liters per minute, the switch pressure is set to 16 psi. If the flow rate falls between 2.5 and 3.5 liters per minute, the switch pressure remains at its present value. This condition provides a hysteresis effect to prevent excessive changing of switch pressure.

Figure 4:
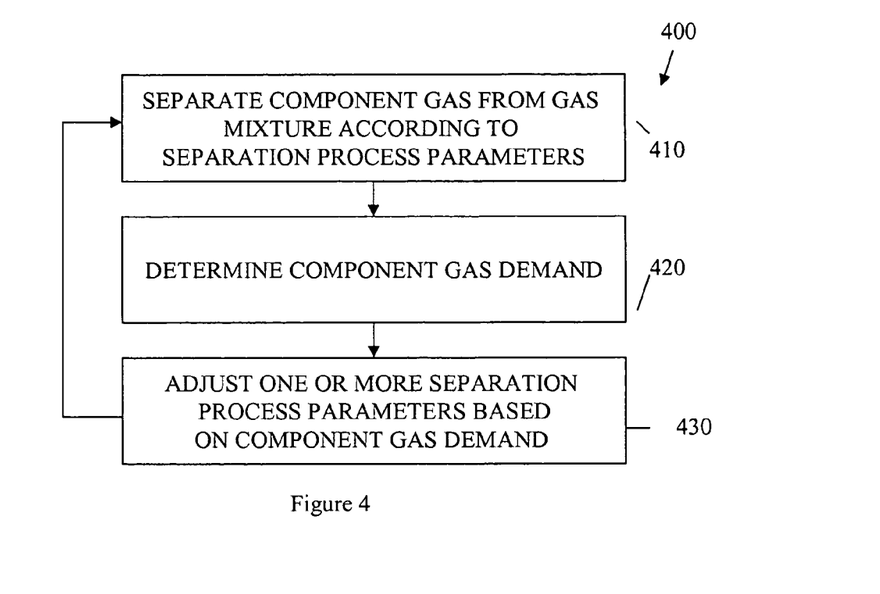
FIG. 4 is a flowchart that outlines a procedure for adjusting parameters of component gas separation based on component gas demand according to an embodiment of the present invention.
Figure 5:
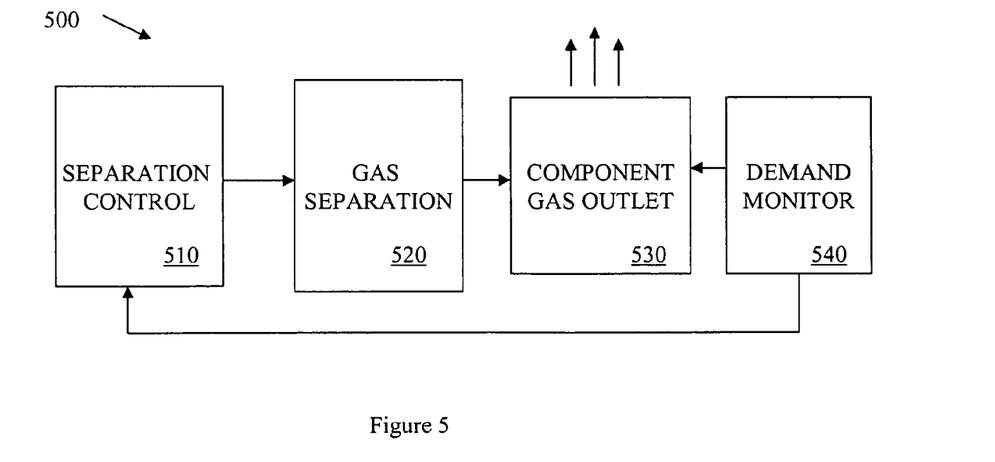
FIG. 5 is a block diagram of a gas separation system that adjusts operating parameters based on component gas demand.

FIGS. 4 and 5 outline the function and components of a concentrator that adjusts its separating process based on patient demand. FIG. 4 illustrates a procedure 400 in which at 410 component gas is separated from an incoming gas mixture according to separation process parameters, such as, for example, the bed switch pressure. The component gas can include a relatively large quantity of a desired product gas such as oxygen and smaller residual amounts of other gases such as argon, neon, and xenon. The component gas demand is determined at 420 and at 430 one or more separation process parameters is adjusted based on the demand. The concentrator 500 shown in FIG. 5 includes a gas separation module 520 that is controlled by separation controller 510. Component gas flows through an outlet 530. The demand for the component gas is monitored by a demand monitor 540 and this demand is fed back to the controller 510 for use in controlling separation.

While the apparatus and method of providing a concentrated product gas has been illustrated by the description of embodiments thereof, and while the embodiments have been described in considerable detail, it is not the intention of this specification to restrict or in any way limit the scope of the appended claims to such detail. Therefore, the apparatus and method of providing a concentrated product gas, in its broader aspects, is not limited to the specific details, the representative apparatus, and illustrative examples shown and described. Accordingly, departures may be made from such details without departing from the spirit or scope of the applicant's general concept for the apparatus and method of providing a concentrated product gas.

The invention claimed is:

1. A method of providing a breathing gas comprising:
   separating a component gas from a gas mixture;
   determining a rate of flow of the component gas, wherein this step comprises:
      measuring at least a first and a second pressure associated with the output of a component gas tank, wherein the first and second pressure measurements are made separate in time and when substantially no component gas enters the tank;
      comparing the first and second pressure measurements and correlating the first and second pressure comparison to a rate of flow of component gas; and
   adjusting the separation of the component gas from the gas mixture based on the rate of flow of the component gas.

2. The method of claim 1 wherein comparing the first and second pressure measurements comprises determining a decay in component gas pressure.

3. The method of claim 1 wherein the step of separating a component gas from a gas mixture is performed by passing the gas mixture alternately through one of a plurality of pressure swing adsorption sieves and wherein the step of adjusting the separation of the component gas from the gas mixture is performed by adjusting a duration of time during which the gas mixture is passed through an active sieve.

4. The method of claim 1 wherein the step of separating a component gas from a gas mixture is performed with a gas separating system that includes a pair of pressure swing adsorption sieve beds that alternately separate the component gas from the gas mixture, wherein an inlet of each sieve bed is selectively connected, via a crossover valve, to an exhaust port and a pressurized gas source, and wherein an outlet of each sieve bed is selectively connected to a component gas outlet and further wherein the outlet of each sieve bed is selectively connected to the outlet of the other sieve bed by a pressure equalization valve and wherein the gas separating system periodically performs a sieve bed switching cycle comprising actuating the pressure equalization valve for a pressure equalization actuation period such that output component gas from an active sieve bed is used to flush byproducts from an inactive sieve bed and actuating the crossover valve to connect the inactive bed to the pressurized gas source and the active bed to the exhaust port;
   and wherein the step of adjusting the separation of the component gas is performed by commencing the switching cycle when the present pressure reaches a target component gas pressure.

5. The method of claim 2 wherein the step of determining a decay comprises determining a rate of decay of component gas pressure during at least a portion of the pressure equalization valve actuation period.

6. The method of claim 5 wherein the rate of decay of component gas is determined by comparing the first pressure measured just after opening of the pressure equalization valve to the second pressure measured after closing of the pressure equalization valve.

7. The method of claim 4 further comprising the step of selecting a target component gas pressure selecting a first target component gas pressure when the present component gas pressure exceeds a first threshold component gas pressure and selecting a second target component gas pressure when the present component gas pressure is below a second threshold component gas pressure.

8. The method of claim 7 wherein the first target component gas pressure is greater than the second target component gas pressure.

9. The method of claim 1 wherein the first pressure measurement comprises a pressure measurement when a pressure equalization valve is substantially open.

10. The method of claim 1 wherein the second pressure measurement comprises a pressure measurement when a pressure equalization valve is substantially closed.

11. The method of claim 9 wherein the second pressure measurement comprises a pressure measurement when the pressure equalization valve is substantially closed.

12. The method of claim 1 wherein the first and second pressure measurements are made only when substantially no component gas enters the tank.

13. A system for separating a component gas from a gas mixture comprising:
   a gas mixture compressor;
   a component gas separator that separates component gas from the gas mixture;
   a component gas tank having an output;
   a pressure sensor associated with the output of the component gas tank;
   a controller comprising logic configured to:
      measure a first and a second pressure from the pressure sensor wherein the first and second pressure measurements are measured when substantially no component gas enters the tank; and
      compare the first and second pressure measurements and correlate the first and second pressure comparison to a rate of flow of component gas; and
   wherein the component gas separator adjusts at least one operation parameter based on the rate of flow of component gas.

14. The method of claim 13 wherein the first and second pressure measurements are made only when substantially no component gas enters the tank.

15. The system of claim 14 wherein the component gas separator includes at least two pressure swing adsorption sieves that alternately separate the gas mixture according to a sieve timing scheme and wherein the gas separator adjusts the timing scheme based on the component gas flow rate.

16. The system of claim 14 wherein the logic to compare the first and second pressure measurements comprises logic to determine a decay in pressure.

17. The system of claim 14 comprising:
a component gas outlet that supplies component gas to a user;
wherein the component gas separator comprises:
a pair of pressure swing adsorption sieve beds each having a sieve inlet that is selectively connected to a source of pressurized atmospheric gas and an exhaust vent and a sieve outlet that is selectively connected to the component gas outlet;
a pressure equalization valve disposed between the sieve outlets that selectively connects the outlets of the sieve beds to one another during a pressure equalization valve actuation period;
a crossover valve disposed between the sieve inlets that selectively connects one of the sieve beds to the exhaust port and the other of the sieve beds to the pressurized atmospheric gas source;
a sieve bed switching cycle controller adapted to actuate the pressure equalization valve to place the sieve outlets in communication with one another when the present component gas pressure reaches a target component gas pressure and to actuate the crossover valve to place an active sieve bed in communication with the exhaust port and an inactive sieve bed in communication with the pressurized atmospheric gas source; and
a target component gas pressure selector that determines a rate of flow of component gas out of the component gas outlet and selects the target component gas pressure based on the rate of flow.

18. The system of claim 17 wherein the sieve bed switching cycle controller comprises a microprocessor having microprocessor-executable instructions stored thereon for actuating the pressure equalization valve when the target component pressure is reached.

19. The system of claim 17 wherein the target component gas pressure selector comprises a microprocessor having microprocessor-executable instructions stored thereon for:
determining a rate of decay of component gas outlet pressure during at least a portion of the pressure equalization valve actuation period;
correlating the rate of decay to a rate of flow of component gas out of the component gas outlet; and
selecting a target component gas pressure based on the rate of flow of component gas.

20. A method of providing a breathing gas comprising:
separating a component gas from a gas mixture;
determining a rate of flow of the component gas, wherein this step comprises:
measuring at least a first and a second pressure associated with the output of a component gas tank, wherein the first and second pressure measurements are made separate in time and based on the state of a pressure equalization valve;
comparing the first and second pressure measurements and correlating the first and second pressure comparison to a rate of flow of component gas; and
adjusting the separation of the component gas from the gas mixture based on the rate of flow of the component gas.

21. The method of claim 20 wherein the first pressure measurement comprises a pressure measurement when the pressure equalization valve is substantially open.

22. The method of claim 20 wherein the second pressure measurement comprises a pressure measurement when the pressure equalization valve is substantially closed.

23. The method of claim 21 wherein the second pressure measurement comprises a pressure measurement when the pressure equalization valve is substantially closed.

* * * * *

UNITED STATES PATENT AND TRADEMARK OFFICE
CERTIFICATE OF CORRECTION

PATENT NO. : 7,722,700 B2 Page 1 of 1
APPLICATION NO. : 11/522683
DATED : May 25, 2010
INVENTOR(S) : Thomas Sprinkle It is certified that error appears in the above-identified patent and that said Letters Patent is hereby corrected as shown below:

In column 7, line 1, the word "method" should read --system--.
    In column 7, line 4, the number "14" should read --13--.
    In column 7, line 9, the number "14" should read --13--.
    In column 7, line 12, the number "14" should read --13--.

Signed and Sealed this

Fifth Day of October, 2010

David J. Kappos
*Director of the United States Patent and Trademark Office*